(12) United States Patent
Early et al.

(10) Patent No.: US 6,455,888 B1
(45) Date of Patent: *Sep. 24, 2002

(54) MEMORY CELL STRUCTURE FOR ELIMINATION OF OXYNITRIDE (ONO) ETCH RESIDUE AND POLYSILICON STRINGERS

(75) Inventors: Kathleen R. Early, Santa Clara, CA (US); Michael K. Templeton, Atherton, CA (US); Nicholas H. Tripsas, San Jose, CA (US); Maria C. Chan, San Jose, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/506,298

(22) Filed: Feb. 17, 2000

Related U.S. Application Data (60) Division of application No. 09/033,836, filed on Mar. 3, 1998, now Pat. No. 6,110,833, which is a continuation-in-part of application No. 09/009,909, filed on Jan. 21, 1998, now Pat. No. 5,939,750.

(51) Int. Cl.[7] .............................................. H01L 29/788

(52) U.S. Cl. ........................................ 257/315; 438/701

(58) Field of Search ........................... 257/315; 438/701

(56) References Cited

U.S. PATENT DOCUMENTS

| | | | |
|---|---|---|---|
| 3,897,274 A | 7/1975 | Stehlin et al. |
| 4,104,090 A | 8/1978 | Pogge |
| 4,105,805 A | 8/1978 | Glendinning et al. |
| 4,300,279 A | 11/1981 | Wieder |
| 4,814,285 A | 3/1989 | Matlock et al. |

(List continued on next page.)

OTHER PUBLICATIONS

Wolf, S. et al, Silicon Processing for the VLSI Era, vol. 1: Process Technology, 1986, Lattice Press, pp. 551–7.*

"High–Density Plasma CVD and CMP for 0.25–µm Intermetal Dielectric Processing." *Solid State Technology*, J.T. Pye, H.W. Fry, W.J. Schaffer, Dec. 1995, pp. 65–71.

"A Four–Metal Layer, High Performance Interconnect System for Bipolar and BiCMOS Circuits". *Solid State Technology.* S. Wilson, J. Freeman, Jr., C. Tracy, Nov. 1991, 67–71.

"Interconnect Metallization For Future Device Generations".*Solid State Technology.* B. Roberts, A. Harrus, R. Jackson, Feb. 1995, pp. 69–77.

*Primary Examiner*—Olik Chaudhuri
*Assistant Examiner*—Howard Weiss
(74) *Attorney, Agent, or Firm*—Amin & Turocy, LLP (57) ABSTRACT

A method for fabricating a first memory cell and a second memory cell electrically isolated from each other is provided. A first polysilicon (poly I) layer is formed on an oxide coated substrate. Then, a sacrificial oxide layer and nitride layer are formed for masking the poly I layer. At least a portion of the masking layer is etched to pattern the first memory cell and the second memory cell and an unmasked portion therebetween. The unmasked portion of the poly I layer is transformed into an insulator via thermal oxidation such that the insulator separates a floating gate of the first memory cell from a floating gate of the second memory cell. The insulator is etched so as to form a gap having gradually sloping sidewalls between a floating gate of the first memory cell and a floating gate of the second memory cell, the gap isolating the floating gate of the first memory cell from the floating gate of the second memory cell. Thereafter, an interpoly dielectric layer and a second polysilicon (poly II) layer are formed substantially free of abrupt changes in step height.

11 Claims, 10 Drawing Sheets

U.S. PATENT DOCUMENTS

| | | | |
|---|---|---|---|
| 4,923,715 A | | 5/1990 | Matsuda et al. |
| 5,316,959 A | | 5/1994 | Kwan et al. |
| 5,342,801 A | | 8/1994 | Perry et al. |
| 5,346,842 A | | 9/1994 | Bergemont |
| 5,378,648 A | | 1/1995 | Lin et al. |
| 5,427,967 A | | 6/1995 | Sadjadi et al. |
| 5,427,968 A | * | 6/1995 | Hong .................. 438/264 |
| 5,432,112 A | * | 7/1995 | Hong .................. 257/315 |
| 5,436,175 A | | 7/1995 | Nakato et al. |
| 5,461,001 A | | 10/1995 | Kurtz et al. |
| 5,468,657 A | | 11/1995 | Hsu |
| 5,589,407 A | | 12/1996 | Meyyappan et al. |
| 5,661,068 A | | 8/1997 | Hirao et al. |
| 5,668,034 A | | 9/1997 | Sery et al. |
| 5,679,474 A | | 10/1997 | Yamagata et al. |
| 5,682,052 A | | 10/1997 | Hodges et al. |
| 5,686,342 A | | 11/1997 | Lee |
| 5,705,420 A | | 1/1998 | Ema |
| 5,892,257 A | * | 4/1999 | Acocella et al. .......... 257/316 |
| 5,933,735 A | | 8/1999 | Wen |
| 5,939,750 A | * | 8/1999 | Early .................. 257/321 |
| 5,973,353 A | * | 10/1999 | Yang et al. .............. 257/315 |

* cited by examiner

MEMORY CELL STRUCTURE FOR ELIMINATION OF OXYNITRIDE (ONO) ETCH RESIDUE AND POLYSILICON STRINGERS

This application is a divisional patent application of U.S. patent application Ser. No. 09/033,836, filed Mar. 3, 1998, now U.S. Pat. No. 6,110,833, entitled ELIMINATION OF OXYNITRIDE (ONO) ETCH RESIDUE AND POLYSILICON STRINGERS THROUGH ISOLATION OF FLOATING GATES ON ADJACENT BITLINES BY POLYSILICON OXIDATION, which is a continuation-in-part of U.S. patent application Ser. No. 09/009,909, filed Jan. 21, 1998 entitled USE OF IMPLANTED IONS TO REDUCE OXIDE-NITRIDE-OXIDE (ONO) ETCH RESIDUE AND POLYSTRINGERS, which issued as U.S. Pat. No. 5,939,750.

FIELD OF THE INVENTION

The present invention generally relates to integrated circuits and, in particular, to a method of memory device fabrication which improves memory cell reliability and manufacturability by preventing formation of poly stringers caused by an oxide-nitride-oxide (ONO) fence.

BACKGROUND OF THE INVENTION

Semiconductor devices typically include multiple individual components formed on or within a substrate. Such devices often comprise a high density section and a low density section. For example, as illustrated in prior art FIG. 1, a memory device such as a flash memory 10 comprises one or more high density core regions 12 and a low density peripheral portion 14 on a single substrate 16. The high density core regions 12 typically consist of at least one M×N array of individually addressable, substantially identical memory cells and the low density peripheral portion 14 typically includes input/output (I/O) circuitry and circuitry for selectively addressing the individual cells (such as decoders for connecting the source, gate and drain of selected cells to predetermined voltages or impedances to effect designated operations of the cell such as programming, reading or erasing).

Figure 2:
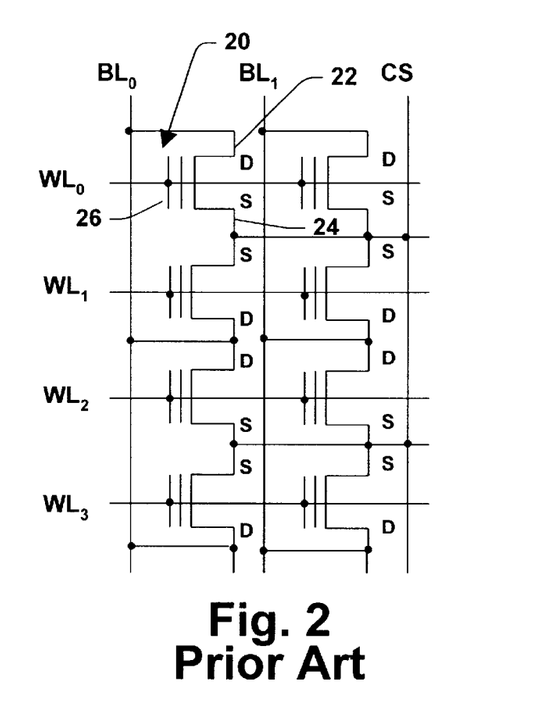
FIG. 2 is a schematic diagram illustrating a prior art core portion of a memory circuit.

The memory cells within the core portion 12 are coupled together in a circuit configuration, such as that illustrated in prior art FIG. 2. Each memory cell 20 has a drain 22, a source 24 and a stacked gate 26. Each stacked gate 26 is coupled to a word line ($WL_0$, $WL_1$, ..., $WL_N$) while each drain 22 is coupled to a bit line ($BL_0$, $BL_1$, ..., $BL_N$). Lastly, each source 24 is coupled to a common source line CS. Using peripheral decoder and control circuitry, each memory cell 20 can be addressed for programming, reading or erasing functions.

Figure 1:
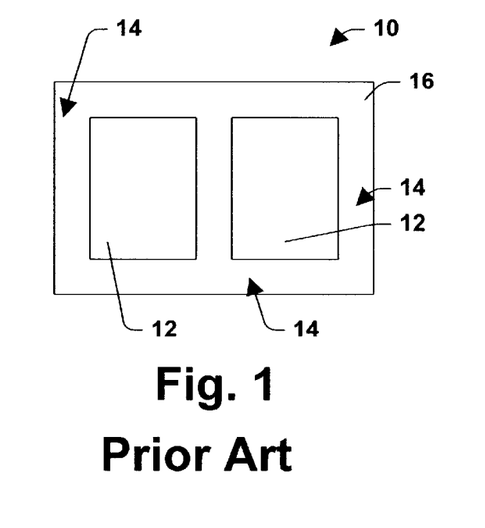
FIG. 1 is a plan view schematically illustrating a prior art layout of a memory device.
Figure 3:
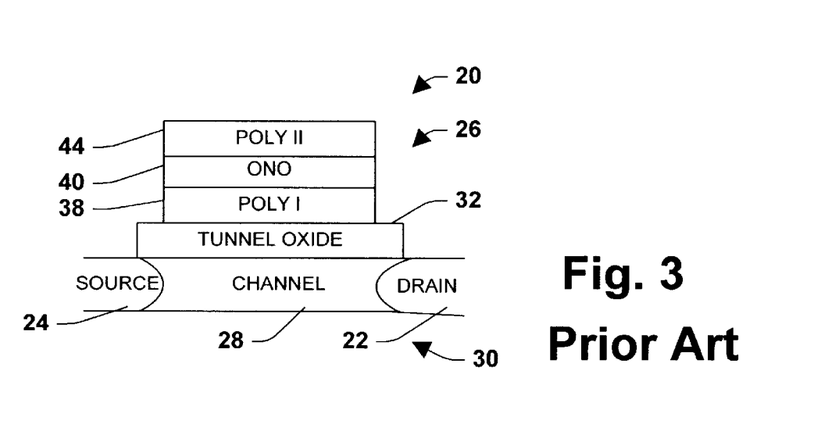
FIG. 3 is a partial cross-sectional view of a prior art stacked gate memory cell.

Prior art FIG. 3 represents a fragmentary cross-sectional diagram of a typical memory cell 20 in the core region 12 of prior art FIGS. 1 and 2. Such a memory cell 20 typically includes the source 24, the drain 22 and a channel 28 in a substrate 30; and the stacked gate structure 26 overlying the channel 28. The stacked gate 26 includes a thin gate dielectric layer 32 (commonly referred to as the tunnel oxide) formed on the surface of the substrate 30. The tunnel oxide layer 32 coats a portion of the top surface of the silicon substrate 30 and serves to support an array of different layers directly over the channel 28. The stacked gate 26 includes a lower most or first film layer 38, such as doped polycrystalline silicon (polysilicon or poly I) layer which serves as a floating gate 38 that overlies the tunnel oxide 32. On top of the poly I layer 38 is an interpoly dielectric layer 40. The interpoly dielectric layer 40 is often a multilayer insulator such as an oxide-nitride-oxide (ONO) layer having two oxide layers sandwiching a nitride layer, or in the an alternative can be another dielectric layer such as tantalum pentoxide. Finally, the stacked gate 26 includes an upper or second polysilicon layer (poly II) 44 which serves as a polysilicon control gate overlying the ONO layer 40. The control gates 44 of the respective cells 20 that are formed in a given row share a common word line (WL) associated with the row of cells (see, e.g., prior art FIG. 2). In addition, as highlighted above, the drain regions 22 of the respective cells in a vertical column are connected together by a conductive bit line (BL). The channel 28 of the cell 20 conducts current between the source 24 and the drain 22 in accordance with an electric field developed in the channel 28 by the stacked gate structure 26.

According to conventional operation, the memory cell 20 (e.g., flash memory cell) operates in the following manner. The memory cell 20 is programmed by applying a relatively high voltage $V_G$ (e.g., approximately 12 volts) to the control gate 38 and a moderately high voltage $V_D$ (e.g., approximately 9 volts) to the drain 22 in order to produce "hot" (high energy) electrons in the channel 28 near the drain 22. The hot electrons accelerate across the tunnel oxide 32 and into the floating gate 34 and become trapped in the floating gate 38 because the floating gate 38 is surrounded by insulators (the interpoly dielectric 40 and the tunnel oxide 32). As a result of the trapped electrons, a threshold voltage ($V_T$) of the memory cell 20 increases by about 3 to 5 volts. This change in the threshold voltage (and thereby the channel conductance) of the memory cell 20 created by the trapped electrons is what causes the memory cell 20 to be programmed.

To read the memory cell 20, a predetermined voltage $V_G$ that is greater than the threshold voltage of an unprogrammed memory cell, but less than the threshold voltage of a programmed memory cell, is applied to the control gate 44. If the memory cell 20 conducts, then the memory cell 20 has not been programmed (the memory cell 20 is therefore at a first logic state, e.g., a zero "0"). Conversely, if the memory cell 20 does not conduct, then the memory cell 20 has been programmed (the memory cell 20 is therefore at a second logic state, e.g., a one "1"). Thus, each memory cell 20 may be read in order to determine whether it has been programmed (and therefore identify the logic state of the memory cell 20).

In order to erase the memory cell 20, a relatively high voltage $V_S$ (e.g., approximately 12 volts) is applied to the source 24 and the control gate 44 is held at a ground potential ($V_G$=0), while the drain 22 is allowed to float. Under these conditions, a strong electric field is developed across the tunnel oxide 32 between the floating gate 38 and the source region 24. The electrons that are trapped in the floating gate 38 flow toward and cluster at the portion of the floating gate 38 overlying the source region 24 and are extracted from the floating gate 38 and into the source region 22 by way of Fowler-Nordheim tunneling through the tunnel oxide 32. Consequently, as the electrons are removed from the floating gate 38, the memory cell 20 is erased.

Figure 4:
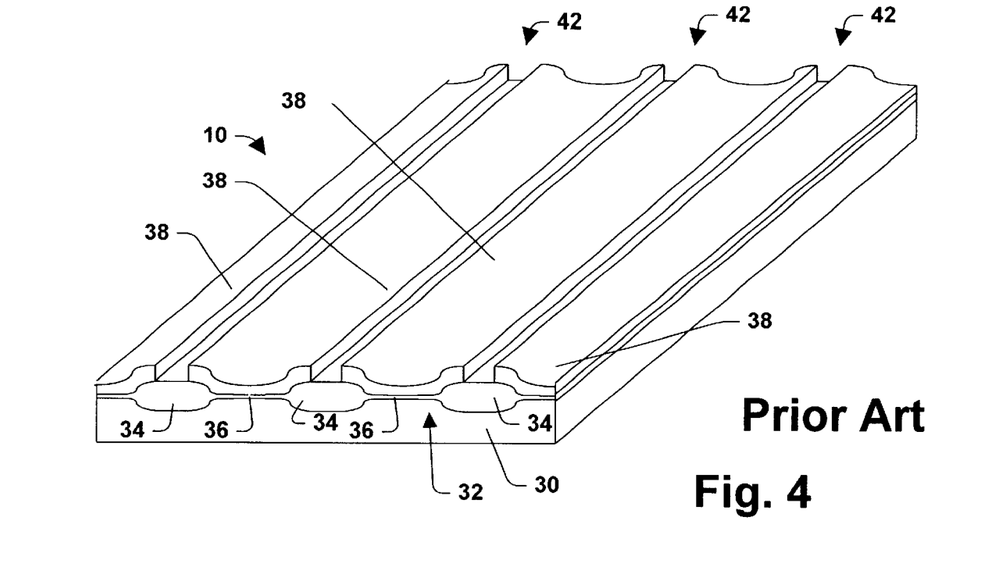
FIG. 4 is a perspective illustration of a portion of a prior art memory device at an early stage in fabrication.
Figure 5:
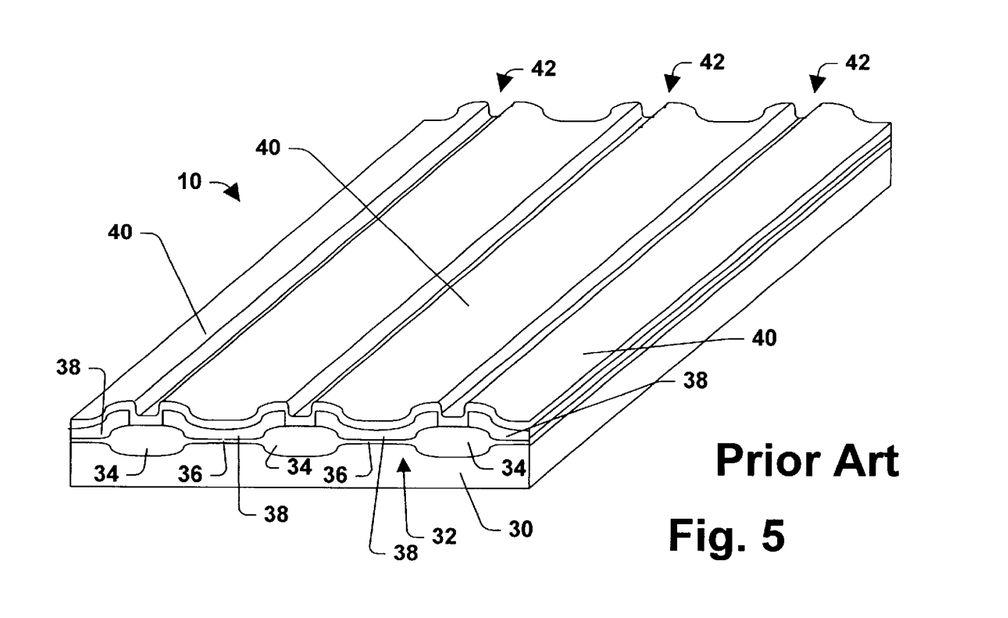
FIG. 5 is a perspective illustration of the prior art memory device of FIG. 4 after formation of an ONO layer,.

Having described a structural arrangement of the memory cell 20, attention is now brought to fabrication of the memory device 10. FIG. 4 illustrates an overall arrangement of the memory device 10 at an early stage of formation. A substrate 30 is shown which comprises regions of thick oxide (field oxide) 34 and thin oxide (tunnel oxide) 32. The field oxide 34 provides for electrically insulating transistors from one and other. A poly I layer 38 has been laid down over the substrate 30, and sections of the poly I layer 38 have been patterned and masked such that an unmasked portion 42 is etched away using convention photolithographic techniques so as to form a series of poly I layer rows 38. FIG. 5 illustrates an ONO layer 40 laid down over the poly I layer rows 38 and the partially exposed field oxide regions 34 between the rows of poly I layer 38. More particularly, since sections of the poly I layer 38 have been etched away, gaps 42 exist between the rows of poly I layer 38 such that sidewalls of the poly I layer rows become coated with the ONO layer material 40 as it is being deposited. The etching step of the poly I layer 38 causes the ONO layer 40 being deposited thereon to be non-uniform in step height. More specifically, since there are gaps 42 between the rows of poly I layer 38, and since the ONO layer 40 conforms to the topography on which it is deposited, the ONO that lies along the sidewalls of the etched poly I lines is significantly thicker that the ONO on top of either the flat portion of the poly I or the flat portion of the field oxide. It is to be appreciated that the thickness of the ONO layer 40 in the figures is shown to be relatively the same as the other layers for ease of understanding, however, the ONO layer 40 is actually very thin relative to the poly I layer 38 and poly II layer 44 (FIG. 6a).

Figure 6A:
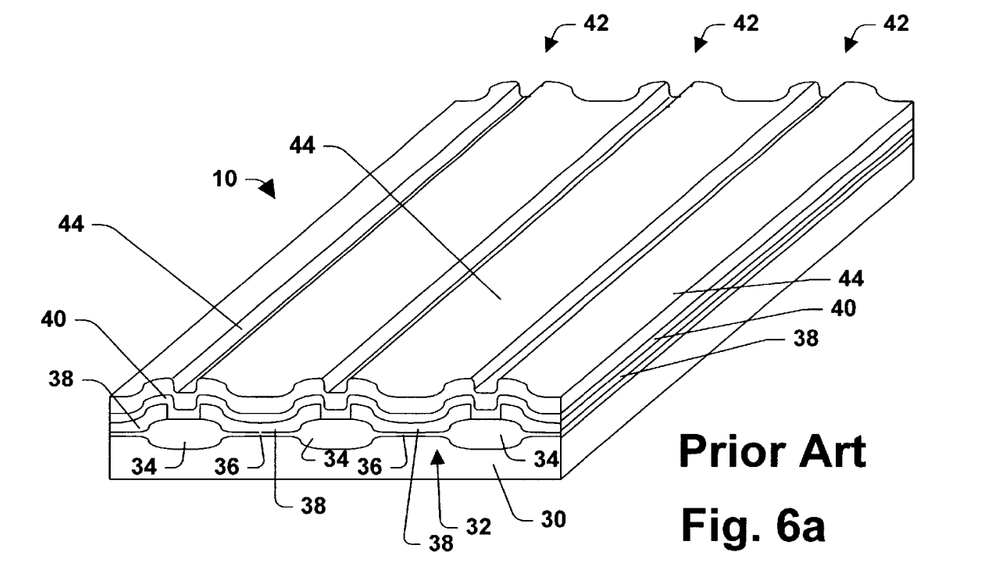
FIG. 6a is a perspective illustration of the prior art memory device of FIG. 5 after formation of a poly II layer.

After application of the ONO layer 40, the poly II layer 44 is laid down over the ONO layer 40 as shown in FIG. 6a. Like the ONO layer 40, the poly II layer 44 also includes undulations as a result of the gaps 42 between rows of the poly I layer 38. The gaps 42 result in the poly II layer 44 being undulated such that portions of the poly II layer 44 adjacent an edge of a respective poly I layer row 38 (where the ONO layer 40 is thickest) is greater in height with respect to the substrate surface 30 than a portion of the poly II layer 44 which lies relatively over other areas. As will be discussed in greater detail below, the gaps 42 may lead to discontinuity in ONO 40 and poly II 44 thickness and even possibly film cracks or breaks.

Figure 6B:
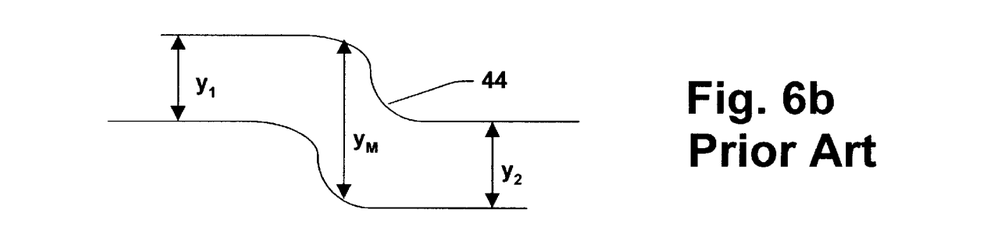
FIG. 6b is a cross-sectional view showing the variation in thickness of the poly II layer in the vicinity of the step in poly I.

FIG. 6b illustrates a substantially large maximum step height ($y_M$) that results because of the undulating poly II layer 44. In particular, the step height of a portion of the poly II layer that lies respectively over a poly I layer row 38 has a step height of $y_1$, and a portion of the poly II layer that lies respectively over the gap 42 between adjacent poly I layer rows has a step height of $y_2$. However, the portion of the poly II layer 44 which represents an undulation (i.e., the transition from the poly II layer lying over the poly I layer row 38 and over the gap 42 between poly I layer rows 38) has a step height of $y_M$, where $y_M$ is substantially greater in height $y_1$ or $y_2$ and results in problems relating to overetch requirements and the formation of an ONO fence as will be discussed in greater detail below.

Figure 7:
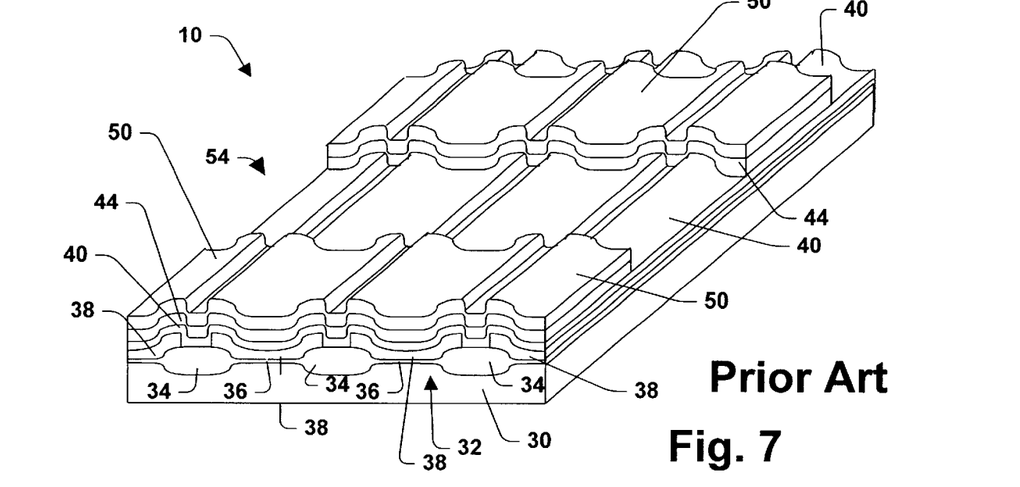
FIG. 7 is a perspective illustration of the prior art memory device of FIG. 6a after a resist layer has been laid down and portions of the poly II layer have been etched away.

Referring now to FIG. 7, a resist 50 is lithographically patterned over portions of the poly II layer 44. Then, the poly II layer 44 is etched away at portions not covered by the resist 50, the etched away portion of poly II layer is generally designated at 54.

Figure 8:
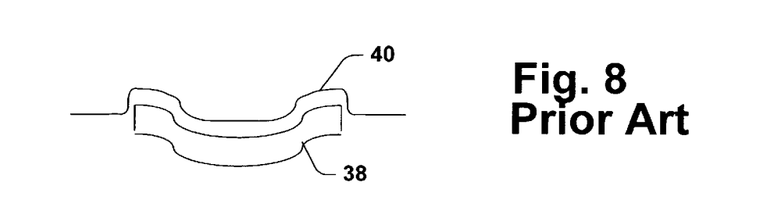
FIG. 8 is a cross-sectional view of the poly I layer, having the ONO layer thereon, of the prior art memory device of FIG. 7.
Figure 9:
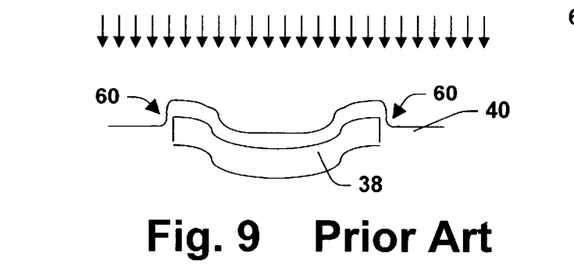
FIG. 9 is a cross-sectional view of the prior art memory device of FIG. 8, wherein the ONO layer is being etched away.
Figure 10:
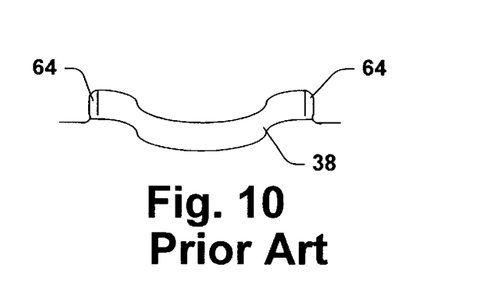
FIG. 10 is a cross-sectional view of the prior art memory device of FIG. 9, depicting an ONO fence remaining along sidewalls of the poly I layer after the ONO etch step.

FIG. 8 is a partial cross-sectional view of the memory device 10 taken at the portion 54. As is seen, the poly II layer 44 has been etched away leaving an ONO layer 40 laid down atop and along vertical sidewalls of the poly I layer 38. The field oxide 34 and tunnel oxide 36 of the substrate 30 are not shown for ease of understanding. In FIG. 9, the ONO layer 40 is shown being substantially etched away using conventional etching techniques. The ONO layer 40 has a substantially greater step height at side wall portions 60 of the poly I layer 38. As a result, these side wall portions of ONO do not become completely etched away and leave what is coined an ONO fence 64 (FIG. 10) along the sidewalls of the poly I layer 38.

Figure 11:
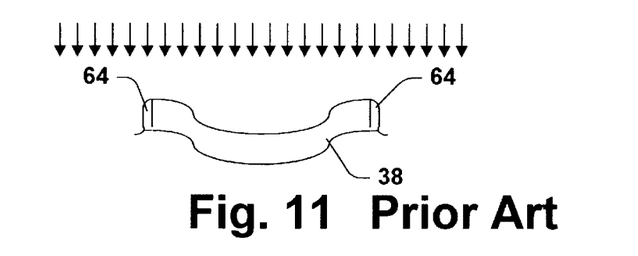
FIG. 11 is a cross-sectional view of the prior art memory device of FIG. 10 wherein the poly I layer is being etched away.
Figure 12:
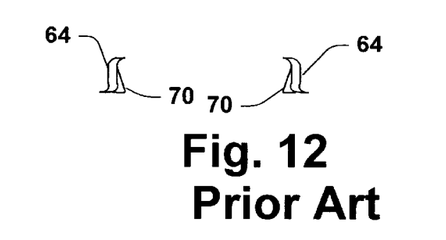
FIG. 12 is a cross-sectional view of the prior art memory device of FIG. 11 wherein the ONO fence shields poly I portions from being etched away during the poly I etch of FIG. 11.
Figure 13:
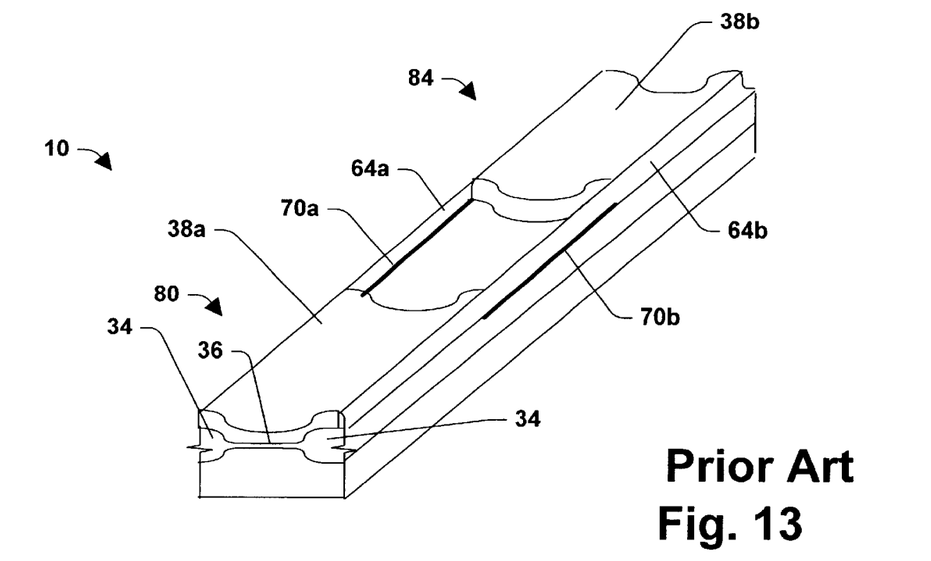
FIG. 13 is a perspective illustration of the prior art memory device of FIG. 12 depicting ONO fences and poly stringers electrically shorting floating gates of adjacent memory cells.

In FIG. 11, the poly I layer 38 is substantially etched away using conventional etching techniques. However, a problem often occurs at this step involving formation of poly stringers. Poly stringers result from incomplete removal of poly I from the unmasked portions of the wafer during etch. The poly stringers of concern here are created during the self-aligned etch (SAE). During the SAE, the ONO 40 and then the poly I 38 between adjacent second gate lines is etched away. In the SAE, the second gate lines act as a mask. This results in substantially perfect alignment of the first gate with the second gate along a direction perpendicular to the second gate lines hence, the name self-aligned etch. During the SAE, the ONO 64 along the sidewalls of the poly I is only partially removed, resulting in the ONO fence. When the poly I 38 is etched, for some memory cells a small "string" of polysilicon is hidden from the etch by the ONO fence. If this happens to even a few cells in the memory the memory chip will not function properly. As shown in FIG. 12, the ONO fence 64 acts as an umbrella and shields portions of the poly I layer 38 from being etched away. These remaining portions of poly I material are known as poly I stringers 70a and 70b as shown in FIG. 13, which may result in electrically shorting adjacent memory cells 20. In other words, the poly I etching step of FIG. 11 serves in part to isolate one memory cell 20 from another. However, if a portion of the poly I layer 38 is not etched away and forms a conductive path (e.g., poly stringer 70) from one memory cell 20 to another, the memory cells 20 will become electrically shorted.

FIG. 13 illustrates in perspective view the ONO fences 64a, 64b that have lead to the formation of poly stringers 70a, 70b which may cause shorting of poly I layers 38a and 38b of two memory cells 20a and 20b, respectively. The polysilicon floating gates 38a and 38b rest on the oxide coated substrate 30. The ONO fences 64a and 64b remain along the sidewalls of the poly I layers 38a and 38b and in the region 80 between the two memory cells 20a and 20b. The additional layers that make up the stacked gate structure 26 of the respective memory cells 20a and 20b are not shown in prior art FIG. 13 for sake of simplicity.

As long as the initial etching of the polysilicon floating gate 38 (which delineates cells 20 along a single word line) occurs in an ideally anisotropic manner, no poly stringers are formed during the second etching of the floating gate 38 (which delineates separate word lines). It is well known, however, that anisotropic etch processes do not repeatably provide ideally anisotropic profiles. Instead, most anisotropic etch processes provide non-ideal profiles in the range of about 85–95° (wherein 90° is ideal). A non-ideal anisotropic etch profile as is illustrated in prior art FIG. 12 leaves an angled ONO fence 64 which acts as an umbrella (or shield) to the poly I etch.

More specifically, when the polysilicon gate 38 is subsequently etched (in an anisotropic manner via, e.g., reactive ion etching (RIE)), as illustrated in prior art FIG. 11, the angled ONO fence 64 shields a portion of the polysilicon gate 38, resulting in remnants of polysilicon, which are the poly stringers 70. Transposing the non-ideally anisotropic etched polysilicon gate 38 and the resulting poly stringers 70 into their macroscopic context (as illustrated in prior art FIG. 13), it is clear that the poly stringers 70 pose a substantial reliability problem since the poly stringers 70 in the etched region 80 can short out the word lines in regions 82 and 84, respectively. That is, instead of the etched region 80 electrically isolating the word lines in regions 82 and 84 from one another, the poly stringers 70 (which are conductive) span the etched region 80 and cause the poly I layers (i.e., floating gates) 38a and 38b in the regions 82 and 84 to be shorted together.

Consequently, in light of the above, it would be desirable to have a method for fabricating a memory cell such that the formation of an ONO fence and resulting poly stringers is eliminated or otherwise substantially reduced.

SUMMARY OF THE INVENTION

The present invention provides for a method of manufacturing a memory cell which mitigates the formation of poly stringers resulting from an ONO fence. ONO fences typically result from an anisotropic etching step which leaves an ONO fence on sidewalls of a poly I layer. As noted above, the ONO fence can result in the formation of poly stringers which will short adjacent memory cells. The present invention first oxidizes portions of the poly I layer and then etches away the oxidized poly I portions so that the sidewalls of the remaining poly I layer portions are gradually sloping rather than steep. As a result, a subsequently deposited ONO layer will have a substantially uniform thickness and thus can be cleanly etched. Therefore, when the ONO etch is performed an ONO fence does not result which in turn prevents poly stringers from forming. According to the present invention, a poly I layer is masked to pattern future memory cells. In other words, a poly I mask is configured to isolate floating gate regions of memory cells in a desired manner. The unmasked portions of the poly I layer are transformed into insulating portions (e.g., silicon oxide, silicon dioxide) by a suitable technique in accordance with the present invention. The resulting insulating portions are etched away so as to isolate the floating gates of patterned memory cells from one another.

More specifically, since oxidized portions of the poly I layer are etched to result in poly I portions having gently sloping sidewalls, changes in the height of the surface of the wafer result from gentle undulations rather than from substantially abrupt 90° steps. Thus, gaps between adjacent memory cells formed from the etching of the oxidized poly I portions have gently sloping sidewalls as compared to the substantially 90° poly I gap sidewalls of conventional memory cells. Therefore, the present invention provides for deposition of an ONO layer of substantially uniform thickness which mitigates subsequent formation of an ONO fence which might lead to poly I stringers.

Furthermore, because gaps between rows of poly I layer have gradually sloping sidewalls, the ONO layer and poly II layer deposited over the poly I layer do not have abrupt steps, which results in nearly uniform step height of the ONO film as seen by the highly anisotropic poly I etch. As a result of forming a poly II layer without abrupt steps, a maximum step height of the poly II layer is reduced. The reduction in maximum step height of the poly II layer affords for reducing over etch requirements for the poly II material. In other words, since the maximum step height of the poly II layer is reduced, as compared to conventionally fabricated memory devices, less etching of the poly II layer is required.

Figure 14:
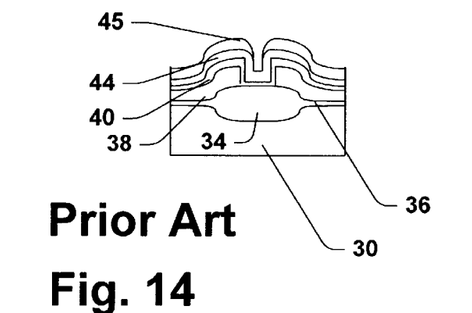
FIG. 14 is a cross-sectional view of a prior art memory device where breaks have occurred in a topside layer.

In addition, the mitigation of abrupt step heights of the various layers by the present invention also results in a second gate stack (e.g., comprising a polysilicon layer, a silicide layer and a topside layer) of low resistance (i.e., less cracks) as compared to second gate stacks fabricated in accordance with conventional techniques. There is an increasing demand for miniaturization in the memory cell industry. This demand has led to an ever constant reduction in separation between memory cells in order to reduce chip size and/or increase density. As a result, gaps between floating gates of adjacent memory cells have become increasingly smaller. However, such gaps still may include steep sidewalls. Consequently, the combination of steep sidewalls and small gap width leads to difficulty in depositing layer material within the small gaps as can be seen in prior art FIG. 14. As a result, portions of layers deposited over such gaps may be weak. In other words, in conventionally fabricated memory devices, breaks, cracks or holes may result in a topside layer 45 and possibly underlying layers at portions lying over the gaps between poly I lines. Therefore, by reducing or eliminating the abrupt step heights the respective layers are less susceptible to cracks and as a result exhibit low resistance.

Thus, the present invention improves memory cell reliability and manufacturability by preventing formation of poly I stringers caused by an ONO (oxide-nitride-oxide) fence, provides for reduction of over etch requirements of gate structure layer materials (e.g., poly II layer) and affords for a second gate stack having low resistance.

In accordance with one specific aspect of the present invention, a method for fabricating a first memory cell and a second memory cell electrically isolated from each other is provided. A first polysilicon (poly I) layer is formed on an oxide coated substrate. The poly I layer is masked to pattern floating gates of the first memory cell and the second memory cell and an unmasked portion therebetween. The unmasked portion of the poly I layer is transformed into an insulator via thermal oxidation. The insulator is etched so as to form a gap having gradually sloping sidewalls between a floating gate of the first memory cell and a floating gate of the second memory cell.

According to another specific aspect of the present invention, a group of memory cells is provided. The group includes a first memory cell and a second memory cell, the first and second memory cells each including a poly silicon (poly I) layer, the poly I layers serving as floating gates. The group also includes a gap having gently sloped sidewalls to isolate the floating gate of the first memory cell from the floating gate of the second memory cell, the gap being formed by transforming an unmasked portion of the poly I layer into an electrically nonconductive medium via thermal oxidation and etching the electrically nonconductive medium so as to form the gap between the floating gate of the first memory cell and the floating gate of the second memory cell.

In accordance with still another specific aspect of the present invention, a method for fabricating a first memory cell and a second memory cell electrically isolated from each other is provided. A first polysilicon (poly I) layer is formed on an oxide coated substrate. Then, a sacrificial oxide layer and nitride layer are formed for masking the poly I layer. At least a portion of the masking layer is etched to pattern the first memory cell and the second memory cell and an unmasked portion therebetween. The unmasked portion of the poly I layer is transformed into an insulator via thermal oxidation such that the insulator separates a floating gate of the first memory cell from a floating gate of the second memory cell. The insulator is etched so as to form a gap having gradually sloping sidewalls between a floating gate of the first memory cell and a floating gate of the second memory cell, the gap isolating the floating gate of the first memory cell from the floating gate of the second memory cell. Thereafter, an interpoly dielectric layer and a second polysilicon (poly II) layer are formed substantially free of abrupt changes in step height.

Yet another specific aspect of the present invention provides for a method for fabricating a first memory cell and a second memory cell electrically isolated from each other. A first polysilicon (poly I) layer is formed on an oxide coated substrate. The poly I layer is masked to pattern floating gates of the first memory cell and the second memory cell and an unmasked portion therebetween. The unmasked portion of the poly I layer is transformed into an insulator via thermal oxidation; and the insulator is etched.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION OF THE INVENTION

The present invention will now be described with reference to the drawings, wherein like reference numerals are used to refer to like elements throughout.

The present invention first oxidizes portions of a poly I layer and then etches. away the oxidized poly I portions so that the sidewalls of the remaining poly I layer portions are gradually sloping. As a result, a subsequently deposited ONO layer has a substantially uniform thickness and thus can be cleanly etched. Therefore, when an ONO etch is performed an ONO fence does not result which in turn prevents poly stringers from forming. The elimination of the ONO fence prevents the formation of poly stringers which as mentioned above may short out adjacent memory cells. Additionally, the present invention provides a substrate for deposition of the poly II layer that is substantially free of abrupt 90° steps. This results in reduced maximum film thickness or step height for the poly II layer as compared with that of memory cells fabricated in accordance with conventional processes. The reduction in maximum step height of the poly II layer affords for reduced over etching requirements of the poly II layer.

Figure 15:
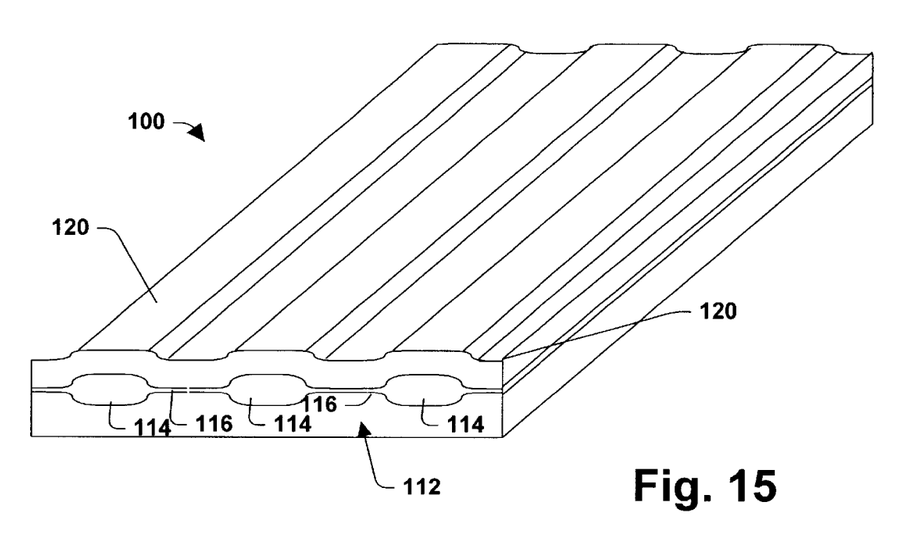
FIG. 15 is a perspective illustration of a portion of a memory device at an early stage in fabrication in accordance with the present invention.

Turning now to FIG. 15, an overall arrangement of a memory device 100 at an early stage of formation is shown in accordance with the present invention. In particular, a silicon substrate 112 is shown comprising field oxide regions 114 and tunnel oxide regions 116. It should be appreciated that although specific layering materials are identified in the preferred embodiment, any materials suitable for carrying out the present invention may be employed and fall within the scope of the claims. A doped polycrystalline silicon (polysilicon or poly I) layer 120 is laid down over the substrate 112. In the present invention, the poly I layer 120 is not etched as is done conventionally. Rather, as will be discussed in greater detail below, portions of the poly I layer 120 are transformed into insulating portions such as for example silicon dioxide. The insulating portions serve as nonconductive isolators between the floating gates (i.e., poly I layers) of adjacent memory cells of the memory device 100.

Figure 16:
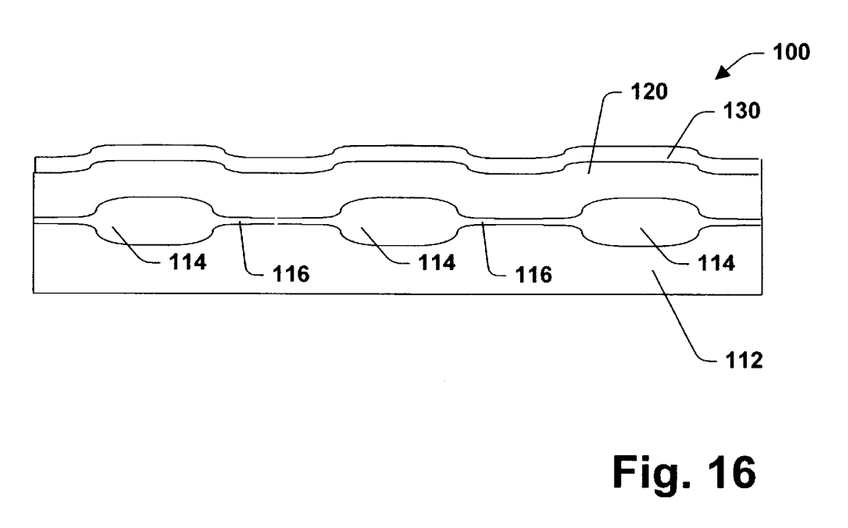
FIG. 16 is a cross-sectional illustration of the memory device of FIG. 15 wherein a sacrificial oxide layer is deposited over a poly I layer in accordance with the present invention.
Figure 17:
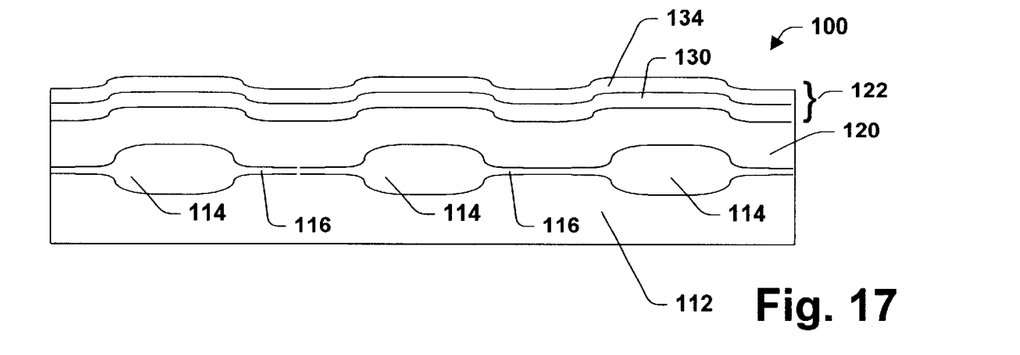
FIG. 17 is a cross-sectional illustration of the memory device of FIG. 16 wherein a nitride layer is deposited over the sacrificial oxide layer in accordance with the present invention.
Figure 18:
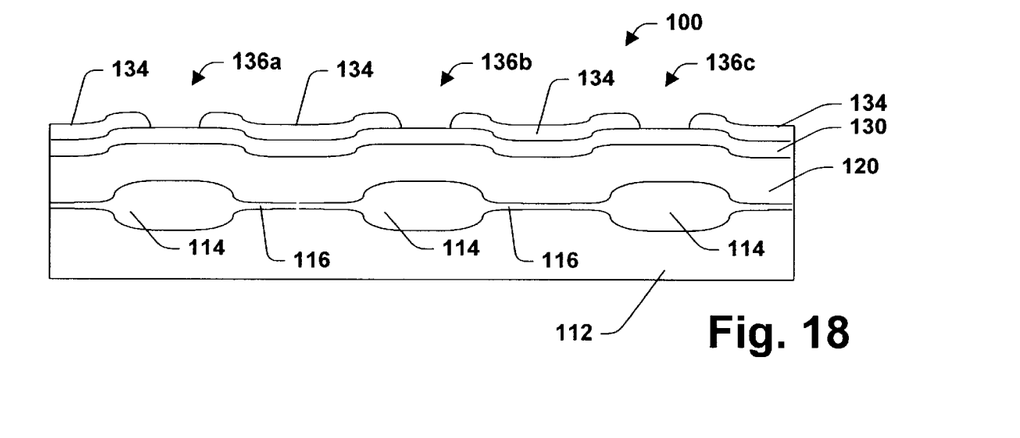
FIG. 18 is a cross-sectional illustration of the memory device of FIG. 17 after portions of the nitride layer have been etched away in accordance with the present invention.

Turning now to FIGS. 16–18, a hard masking layer 122 (FIG. 17) is grown/deposited over the poly I layer 120. In the preferred embodiment, the hard masking layer includes a barrier oxide (i.e., sacrificial oxide layer 130) (FIG. 16) and a nitride layer 134 (FIG. 17) over it. More specifically, an oxide is initially grown/deposited over the poly I layer 120 to form the sacrificial oxide layer 130. The sacrificial oxide layer 130 is employed to compensate for the highly tensile characteristics of the subsequently deposited nitride layer 134. In other words, if the nitride layer 134 was directly deposited on the poly I layer 120, the highly tensile characteristics of the nitride layer 134 might result in damage to the poly I layer 120 during instances of thermal mismatch. However, it is to be appreciated that employment of the sacrificial oxide layer 130 may be omitted if desired. Next, as shown in FIG. 17 the topside layer 134 (e.g., silicon nitride) is grown/deposited over the sacrificial oxide layer 130 to complete the hard masking layer 122. Next suitable photolithography steps are carried out so as to define areas of the silicon nitride layer 134 which are to be etched away. A photoresist (not shown) is lithographically patterned over portions of the nitride layer 134 to define portions of the poly I layer 120 that are to be transformed into insulative material. FIG. 18 illustrates the silicon nitride layer 134 being etched away at portions not covered by the photoresist so as to expose portions of the sacrificial oxide layer 130 and underlying poly I layer 120. As will be readily apparent from the discussion below, the portions of the poly I layer underlying the exposed portions of the sacrificial oxide layer 130 will be oxidized. The nitride layer 134 may be etched away for example by exposing the nitride layer to an HF dip to remove any oxide that may have formed over the nitride layer 134. Thereafter, a plasma etch is employed to etch the nitride layer.

The exposed portions 136a, 136b and 136c (collectively referred to by reference numeral 136) of the poly I layer 120 will be transformed into insulating material (e.g., silicon dioxide) as will be discussed in greater detail below. The exposed portions 136 will be etched away to leave gaps having gradually sloping sidewalls which will isolate floating gates of adjacent memory cells. As noted above, such isolating was conventionally achieved by etching of the poly I layer to form gaps having steep sidewalls between floating gate lines. However, such etching of the poly I layer contributed to the formation of poly stringers because subsequently deposited ONO was not of uniform thickness. After an ONO etch was performed, areas of thicker ONO were not completely etched away and resulted in formation of an ONO fence which could lead to the formation of poly stringers. In the present invention, such open gaps between adjacent floating gate lines do not have steep sidewalls but rather gently sloping walls so that subsequently deposited ONO will have a substantially uniform thickness (ie., thickness of the ONO is defined as the depth of the ONO perpendicular to the wafer surface) and is more readily etched. Thus, formation of an ONO fence is mitigated which in turn mitigates formation of poly stringers.

After the nitride layer 134 is suitably etched, the photoresist is stripped and suitable pre-oxidation cleaning steps are performed. For example, one method for stripping the photoresist might include employing a dry photoresist strip in an $O_2$ plasma or oxygen plasmastrip and/or a wet clean using sulfuric acid or ammonium hydroxide mixed with ionized water and hydrogen peroxide. It will be appreciated that any suitable method or means for stripping the photoresist and performing preoxidation cleaning may be employed and fall within the scope of the present invention.

Preferably, the oxidation of the exposed poly I portions 136a, 136b and 136c is performed via employment of suitable thermal oxidation techniques. For example, according to one specific aspect of the invention an entire wafer from which the memory device 100 is to be fabricated is placed in a quartz tube in a vertical or horizontal type heat treatment furnace. An oxidizing source such as oxygen and water vapor is fed into the quartz tube, the wafer is heated up (i.e., annealed) to approximately 900° C. and thus the unmasked or exposed portions 136a, 136b and 136c of the poly I layer 120 are oxidized. It is to be appreciated that any suitable oxidation techniques for oxidizing the poly I layer in accordance with the present invention may be employed and fall within the scope of the present invention.

Depending on the thermal budget for a particular device, the anneal may be either a furnace anneal, a rapid thermal anneal (RTA) or any other suitable anneal. As a result of the anneal, the selected portions 136 of the poly I layer 120 (i.e., those portions of the poly I layer not masked by the masking layer 122) are transformed into insulating material.

Figure 19A:
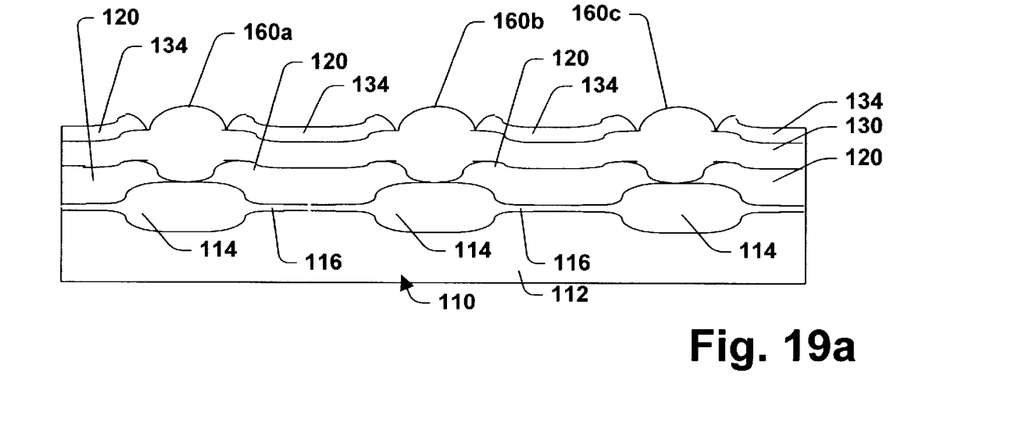
FIG. 19a is a cross-sectional illustration of the memory device of FIG. 18 wherein exposed portions of the sacrificial oxide layer and poly I layer are oxidized in accordance with the present invention.

Referring now to FIG. 19a, the unmasked portions 136 are shown transformed into silicon dioxide ($SiO_2$) via the aforementioned oxidation step. As a result of the oxidation, the unmasked portions 136 are transformed into silicon dioxide portions 160a, 160b and 160c (collectively identified as reference numeral 160). The silicon dioxide portion (s) 160 shall serve to provide for gently sloping sidewalls of the non-oxidized poly I portions 120 after etching of the silicon dioxide portions 160. In particular, the poly I portions 136 will be oxidized in an isotropic manner which results in unoxidized portions of the poly I layer 120 (that lie adjacent the oxidized portions 160) having gently sloping sidewalls.

Figure 19B:
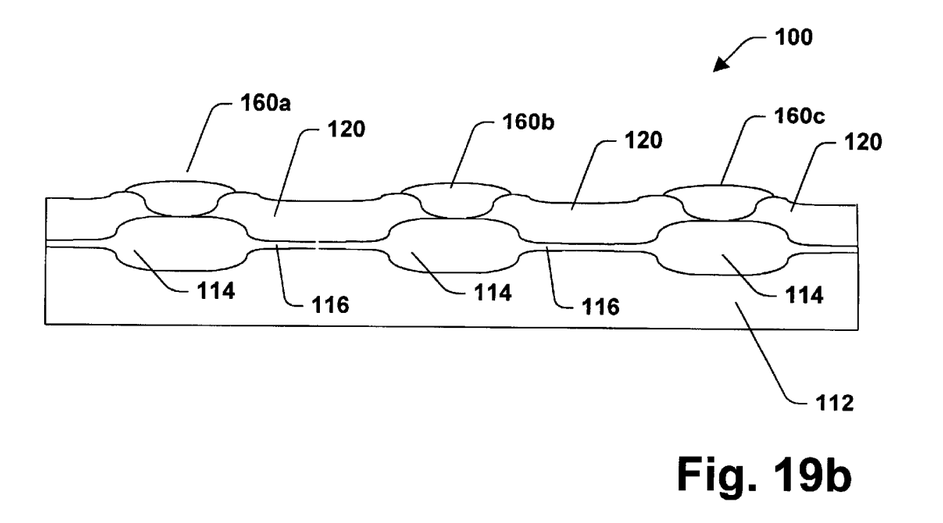
FIG. 19b is a cross-sectional illustration of the memory device of FIG. 19a after the remaining nitride layer portions and the sacrificial oxide layer have been stripped away in accordance with the present invention.

Referring now to FIG. 19b, after the silicon dioxide portions 160 are formed the remaining portions of nitride layer 134 and sacrificial oxide layer 130 are stripped leaving an exposed poly I layer 120 with oxidized portions 160.

Figure 19C:
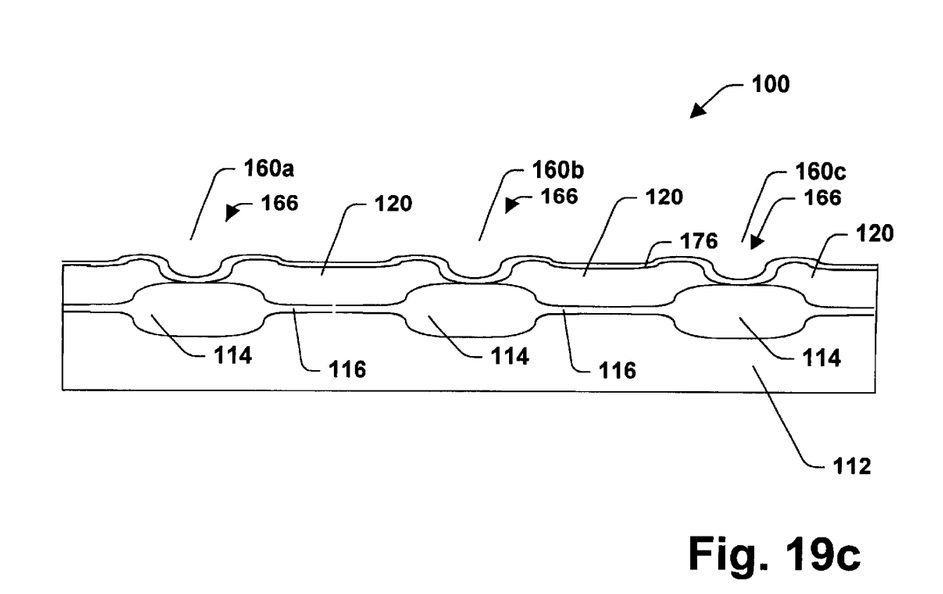
FIG. 19c is a cross-sectional illustration of the memory device of FIG. 19b after the oxidized poly I portions have been etched away and an ONO layer subsequently deposited over the remaining poly I layer and field oxide regions in accordance with the present invention.

Next, the oxidized poly I portions 160 are etched away using suitable etching techniques. As noted above, the oxidation of the poly I portions 160 is substantially isotropic so that when etched away the remaining non-oxidized poly I portions 120 have sidewalls of gently slope. As can be seen in FIG. 19c, an ONO layer 176 subsequently deposited over the poly I layers 120 and the exposed field oxide portions 114 has a substantially uniform thickness as a result of the gradually sloping sidewalls of the poly I portions 120. Thus, the ONO layer 176 will be fully exposed to plasma etch (e.g., substantially free of abrupt steps). In other words since no discrete vertical surfaces are created in the poly I layer 120, the ONO layer 176 is free of abrupt vertical transitions that could create substantial disparity in ONO thickness as in conventionally fabricated memory devices (see e.g., FIG. 5).

An ONO fence is thus prevented from forming along sidewalls of the poly I layer 120. More particularly, ONO is laid down substantially uniformly in thickness because gaps 166 between the poly I lines 120 have gradually sloped sidewalls rather than abrupt sidewalls as in conventional memory cells. The elimination of ONO fence formation results in the avoidance of poly I stringers being formed as a result of an ONO fence shielding portions of the poly I material during an initial etching step as described above. (see e.g., prior art FIG. 14).

Figure 20:
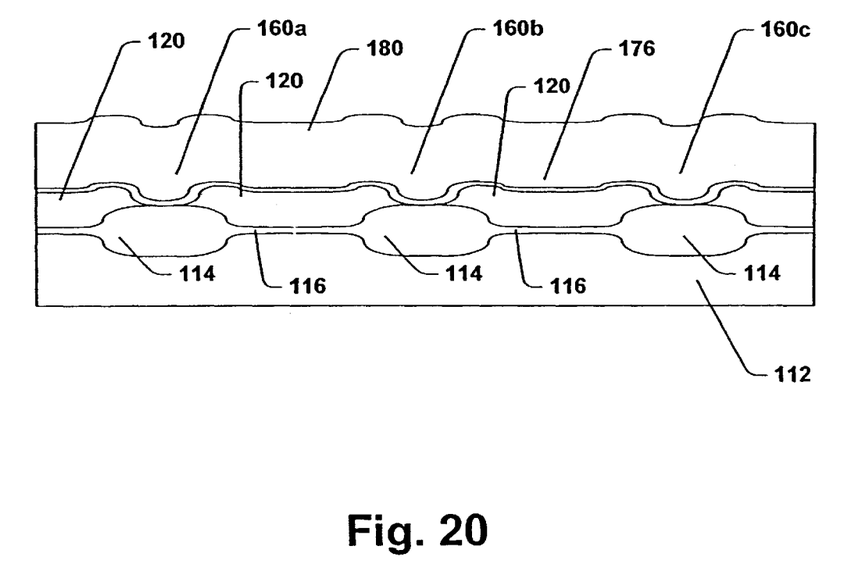
FIG. 20 is a cross-sectional illustration of the memory device of FIG. 19c after a poly II layer has been deposited over the ONO layer in accordance with the present invention.
Figure 21:
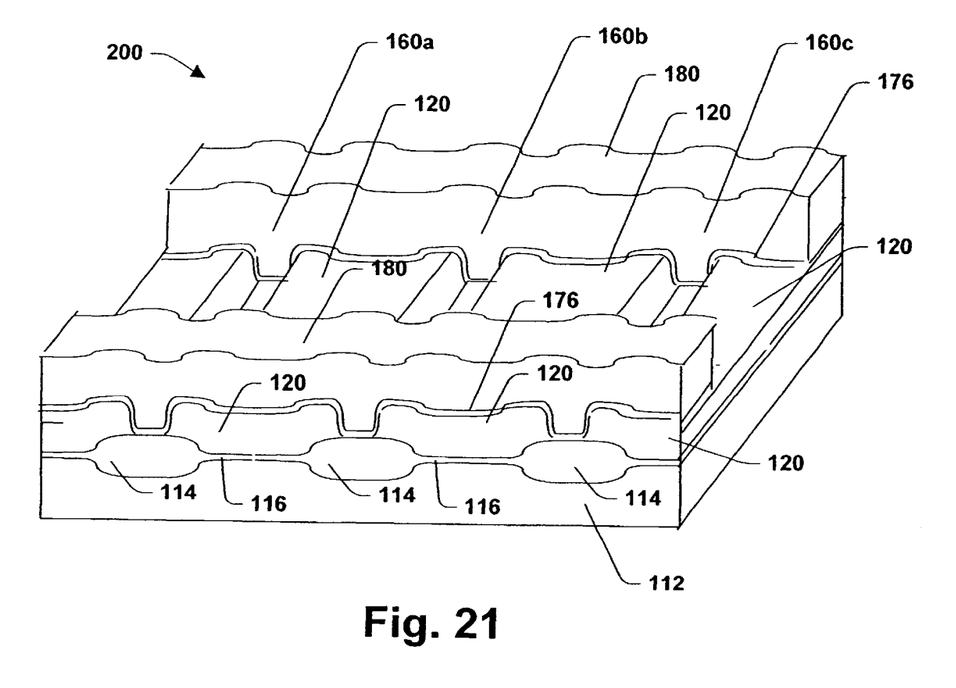
FIG. 21 is a perspective drawing illustrating the memory device of FIG. 20 after an unmasked portion of the poly II layer and ONO layer have been etched away to the poly I layer in accordance with the present invention.
Figure 22:
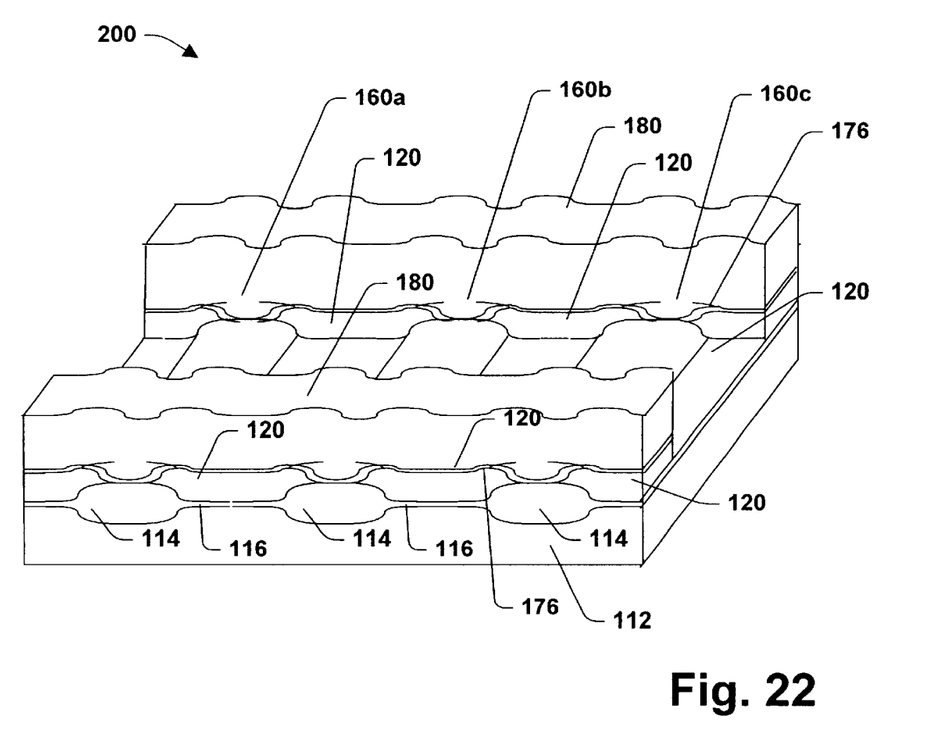
FIG. 22 is a perspective drawing illustrating electrically isolated memory cells after a substantially final etching step in accordance with the present invention.

Turning now to FIGS. 20–22 in consecutive order, a poly II layer 180 is shown being laid down over the ONO layer 176. Because the ONO layer 176 is substantially free of abrupt steps, the poly II layer 180 deposited thereon is also substantially free of abrupt steps. Thereafter, the poly II layer 180 is masked such that unmasked portions 190 of the poly II layer 180 and ONO layer 176 are etched. away using suitable techniques. Finally, the portions of poly I 120 that are unmasked are etched away to leave isolated memory cells 200.

The present invention thus provides for deposition/growth of an ONO layer having substantially uniform thickness which can be fully etched. Therefore, when an ONO etch is performed an ONO fence does not result which in turn prevents poly stringers from forming. Additionally, the present invention provides a substrate for deposition of the poly II layer that is substantially free of abrupt steps. This results in reduced maximum film thickness for the poly II layer as compared with that of memory cells fabricated in accordance with conventional processes. The reduction in maximum film thickness of the poly II layer affords for reduced over etching requirements of the poly II layer. Furthermore, the gently sloping sidewalls of remaining poly I portions of the present invention afford for reducing the formation of cracks in subsequently deposited films.

It will be appreciated that although the present invention is described with respect to forming silicon dioxide insulating portions, any suitable material may be employed as the insulating portions. For example, but not to be considering limiting, the insulating portions may comprise silicon oxide. An exemplary procedure for forming the silicon dioxide portions is explained above, however, any suitable technique for forming silicon dioxide or other suitable insulating material (e.g., $SiO_{x(x \geq 1)}$) may be employed to carry out the present invention and is intended to fall within the scope of the claims.

Furthermore, it is to be appreciated that a partial etch of the poly I layer 120 may be performed prior to oxidation thereof in order to compensate for excessive lateral spreading of the oxidized poly I portions 160 as compared to the thickness of the poly I layer 120.

Those skilled in the art will recognize that the embodiment(s) described above and illustrated in the attached drawings are intended for purposes of illustration only and that the subject invention may be implemented in various ways. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A group of memory cells, comprising:

a first memory cell and a second memory cell, the first and second memory cells each including a poly silicon (poly I) layer, the poly I layers serving as floating gates; and a gap having gently sloped sidewalls to isolate the floating gate of the first memory cell from the floating gate of the second memory cell, the gap being formed by transforming an unmasked portion of the poly I layer into an electrically nonconductive medium via thermal oxidation and etching the electrically nonconductive medium so as to form the gap between the floating gate of the first memory cell and the floating gate of the second memory cell, wherein the slope of the gap sidewalls is such that a layer of material deposited over the floating gates and the gap will be substantially free of abrupt steps.

2. The group of claim 1, wherein the layer of material is oxide-nitride-oxide (ONO) having a substantially uniform thickness after being deposited over the floating gates and the gap.

3. The group of claim 1, the electrically nonconductive medium being $SiO_{x(x \geq 1)}$.

4. The group of claim 1, the first memory cell further including an interpoly dielectric layer and a second polysilicon (poly II) layer.

5. The group of claim 1, the thermal oxidation including a step of furnace oxidation.

6. The group of claim 1, wherein the unmasked poly I material is partially etched prior to thermal oxidation to prevent excess lateral spreading of the oxidized poly I material.

7. A group of memory cells, comprising:

a first floating gate and an adjacent second floating gate, the first and second floating gates forming a substantially U-shaped gap therebetween which facilitates isolating the first floating gate from the second floating gate, the U-shaped gap having gently sloping sidewalls, wherein the slope of the gap sidewalls is such that a layer of material deposited over the floating gates and the gap will be substantially free of abrupt steps.

8. The group of claim 7, wherein the layer of material is oxide-nitride-oxide (ONO) having a substantially uniform thickness after being deposited over the floating gates and the gap.

9. The group of claim 7, a first memory cell further including an interpoly dielectric layer and a second polysilicon (poly II) layer.

10. A group of memory cells, comprising:

a first floating gate and a second floating gate, the first and second floating gates having respective curvilinear surface portions which engage with surface portions of a field oxide region so as to form a gap having gently sloping sidewalls, the gap facilitating isolating a first memory cell from a second memory cell, wherein the slope of the gap sidewalls is such that a layer of material deposited over the floating gates and the gap will be substantially free of abrupt steps.

11. The group of claim 10, wherein the layer of material is oxide-nitride-oxide (ONO) having a substantially uniform thickness after being deposited over the floating gates and the gap.

* * * * *